United States Patent
Drechsler et al.

(10) Patent No.: US 9,612,192 B2
(45) Date of Patent: Apr. 4, 2017

(54) CUVETTE FOR PHOTOMETRIC MEASUREMENT OF SMALL LIQUID VOLUMES

(75) Inventors: Andreas Drechsler, Baar (CH); Rijk Edwin Oosterbroek, Cham (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1010 days.

(21) Appl. No.: 13/325,631

(22) Filed: Dec. 14, 2011

(65) Prior Publication Data
US 2012/0156796 A1 Jun. 21, 2012

(30) Foreign Application Priority Data
Dec. 15, 2010 (EP) .................................... 10195225

(51) Int. Cl.
*G01N 21/00* (2006.01)
*G01N 21/03* (2006.01)

(52) U.S. Cl.
CPC ..... *G01N 21/03* (2013.01); *G01N 2021/0378* (2013.01)

(58) Field of Classification Search
None
See application file for complete search history.

(56) References Cited

U.S. PATENT DOCUMENTS

| 4,560,269 A | 12/1985 | Baldszun et al. |
| 5,571,479 A | 11/1996 | Koch |
| 6,249,345 B1 | 6/2001 | Kraack et al. |
| 7,138,091 B2 | 11/2006 | Lee et al. |
| 2008/0141784 A1 | 6/2008 | Murakami |
| 2010/0238436 A1* | 9/2010 | Havard ......................... 356/246 |

* cited by examiner

*Primary Examiner* — Robert Xu
(74) *Attorney, Agent, or Firm* — Roche Diagnostics Operations, Inc.

(57) ABSTRACT

A cuvette comprising a body having an upper part comprising an upper open top portion and upper walls forming four upper inner edges and an upper open bottom portion with a first substantially rectangular cross-section in a plane A-A; and a lower measurement chamber comprising a lower closed bottom portion and lower walls forming four lower inner edges and a lower open top portion with a second substantially rectangular cross-section in a plane B-B smaller than the first cross-section in the plane A-A. An abrupt transition zone is positioned between the plane A-A and the plane B-B comprising four transition inner edges connecting the four lower inner edges to the upper open bottom portion. At least in the plane B-B the lower inner edges comprise fillets having a first radius (R1). At least in the plane A-A the upper inner edges comprise fillets having a second radius (R2) being larger than (R1).

14 Claims, 6 Drawing Sheets

CUVETTE FOR PHOTOMETRIC MEASUREMENT OF SMALL LIQUID VOLUMES

TECHNICAL FIELD

The present disclosure generally relates to the field of optical cuvettes for photometric measurement of liquids in an optical system and, more particularly, to cuvettes comprising an upper part and a measurement chamber at the bottom. The disclosure also relates to optical systems comprising a cuvette and to methods for using cuvettes in optical systems.

BACKGROUND

Various types of tests related to patient diagnosis and therapy can be performed by analysis of patient fluid samples. For the analysis, such patient samples are typically placed in sample vials, extracted from the vials, combined with various reagents in special reaction cuvettes, incubated, and analyzed. In typical clinical chemistry and some immunochemical analyses, one or more assay reagents are added to a liquid sample, and the sample-reagent combination is mixed and incubated within a reaction cuvette. Photometric measurements using a beam of light illuminating the sample-reagent combinations in such reaction cuvettes are made from which an amount of analyte may be determined using known techniques. Examples of such photometric measurements comprise turbidimetric, fluorometric and absorption measurements or the like.

There is an ever growing need to increase the throughput of said analyses, to make them faster, less expensive, and simpler to perform while at least maintaining, if not increasing, precision and reliability. In order to achieve this goal, substantial effort has been devoted to miniaturization, parallelization, and integration of various process steps, e.g., by processing several cuvettes at a time in a fully automated analyzer comprising pipetting units, reagents and an optical system. Particularly there is a tendency to decrease reaction volumes thus minimizing consumption of samples and reagents, reducing costs and waste volumes.

Conventional cuvettes are optimized for mixing and for the photometric measurement of liquid volumes in the order of 100 μL or more. When trying to use the same cuvettes for smaller volumes, problems arise, such as inefficient mixing and adverse capillary effects. This in turn results in more difficult positioning during optical detection. In particular, as the liquid level becomes lower this makes the photometric measurement unreliable.

When trying to use smaller cuvettes instead, the capillary effects become even more severe than for larger cuvettes due to an increased surface to volume ratio. Thus the measurement is even less reliable.

In case of liquid-surface interfaces characterized by large contact angles, another and rather incontrollable effect may be observed, which is tilting of the liquid surface. For small volumes this may have a significant negative impact on the reliability of the photometric measurement.

SUMMARY

It is against the above background that the embodiments of the present invention provide certain unobvious advantages and advancements over the prior art. In particular, the inventors have recognized a need for improvements in cuvettes for photometric measurement of small liquid volumes.

Although the embodiments of the present invention are not limited to specific advantages or functionality, it is noted that the present disclosure defines a cuvette, which enables reliable and reproducible photometric measurement of small volumes of liquids. This is achieved by providing a cuvette with an optimized geometry and a measurement chamber contained therein, which are configured to maximize the measurement volume.

By enabling operation with smaller volumes, the embodiments of the present invention also enable more tests per sample volume, or running of a test when sample availability is limited. The embodiments of the present invention further provide for the reduced consumption of reagents, meaning lower costs per test and less waste, with benefits for the user and the environment. Also, by reducing sample and reagent volumes, reactions may reach completion more rapidly, thus reducing turn-around time. Further, for reactions requiring heat, equilibration of temperature throughout the sample volume is quick, due to minimized thermal time constants and thermal gradients across the sample. Thus, throughput is also increased.

In one embodiment, a cuvette for photometric measurement of liquids is provided comprising a body having outer walls and an inner space for receiving liquids. The body comprises an upper part, a lower measurement chamber with an inner volume less than about 50 μL, and an abrupt transition zone between the upper part and the lower measurement chamber. The upper part comprises an upper open top portion and an inner surface having in a plane A-A a first annular or substantially rectangular cross-section with four upper inner edges, the upper inner edges extending from the plane A-A to the upper open top portion. The lower measurement chamber comprises a lower closed bottom portion, a lower front wall, a lower back wall, two lower side walls, the lower walls forming four lower inner edges and a lower open top portion with a second substantially rectangular cross-section in a plane B-B smaller than the first annular or substantially rectangular cross-section in the plane A-A, wherein at least the lower front wall and the lower back wall, have portions which are substantially planar and substantially parallel to each other. The transition zone extends between the plane A-A and the plane B-B and comprises four transition inner edges connecting the four lower inner edges to the upper part, wherein the plane A-A is different from the plane B-B. At least in the plane B-B the lower inner edges are sharp or comprise fillets having a first radius. In the plane A-A the first annular cross-section has a second radius or the upper inner edges comprise fillets having a second radius, the second radius being larger than the first radius. The transition inner edges comprise fillets having a gradually increasing radius passing from the sharp edges or the first radius of the lower inner edges in the plane B-B to the second radius of the first annular cross-section or of the upper inner edges in the plane A-A.

In another embodiment, an optical system for photometric measurement of liquids is provided comprising a plurality of cuvettes as described herein, a light source providing a light beam, an optical detector, and a control unit configured to bring one cuvette at a time in optical alignment with the light source and the detector so that the lower front wall faces the light source and the lower back wall faces the optical detector.

In yet another embodiment, an instrument for photometric measurement of liquids is provided comprising an optical system as described herein and a liquid processing unit. The instrument is configured for controlling pipetting, in the lower measurement chamber of a cuvette, a pre-defined volume of liquid or for adding one or more liquids until a pre-defined volume of liquid is reached, which nearly corresponds to the inner volume of the lower measurement chamber.

In still yet another embodiment, a method for photometric measurement of liquids is provided comprising holding a cuvette as described herein in optical alignment with a light source providing a light beam and a detector so that the lower front wall faces the light source and the lower back wall faces the optical detector, and moving the cuvette along an axis parallel to the lower front wall while performing a photometric measurement.

These and other features and advantages of the embodiments of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
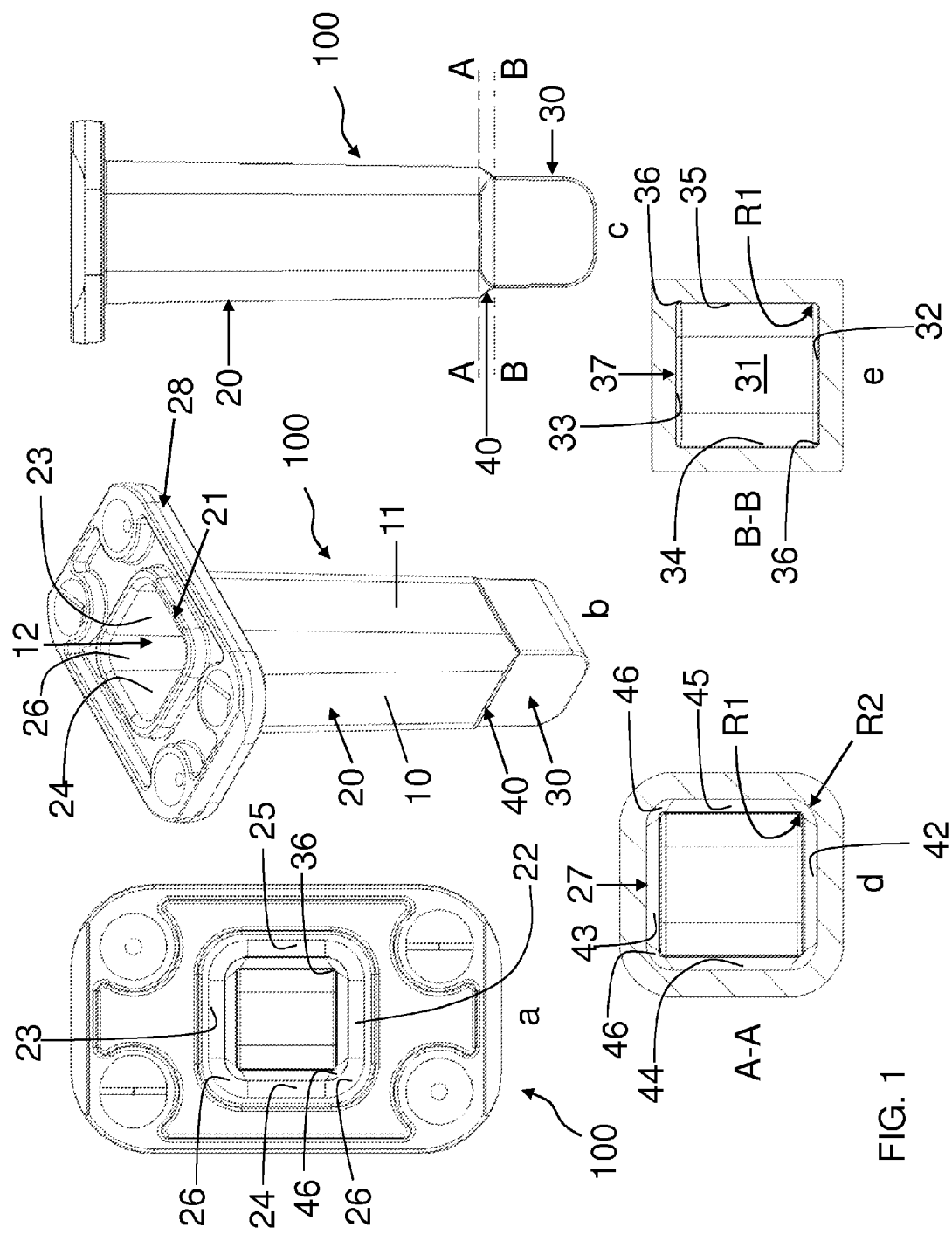
FIGS. 1a to 1e show an embodiment of a cuvette for photometric measurement of liquids.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION

The embodiments of the present invention refer to a cuvette for photometric measurement of liquids. The cuvette comprises a body having outer walls and an inner space for receiving liquids. The body comprises an upper part. The upper part comprises an upper open top portion for allowing liquids to be introduced into the cuvette and an inner surface having in a plane A-A a first annular cross-section or substantially rectangular cross-section with four upper inner edges, the upper inner edges extending from the plane A-A to the upper open top portion.

The body further comprises a lower measurement chamber. The lower measurement chamber comprises a lower closed bottom portion, a lower front wall, a lower back wall, two lower side walls, said lower walls forming four lower inner edges and a lower open top portion with a second substantially rectangular cross-section in a plane B-B smaller than the first annular or substantially rectangular cross-section in the plane A-A. The lower front wall and the lower back wall have portions, which are substantially planar and substantially parallel to each other.

The body further comprises a transition zone, i.e., an abrupt transition zone, between the upper part and the lower measurement chamber, i.e., between the plane A-A and the plane B-B, wherein the plane A-A is different from the plane B-B. The transition zone comprises four transition inner edges connecting the four lower inner edges to the upper part.

The term "substantially rectangular" comprises the term "substantially squared" and is herein used to indicate a geometry formed by at least four edges, at least two of which comprising at least a portion being straight and parallel to each other and wherein at least at the corners the geometry may be smoothed, e.g., present a curvature or radius.

The term "annular" refers primarily to a circular or elliptical geometry and more generally to any area defined by an edgeless curved closed line.

The terms "substantially planar" and "substantially parallel" refer to surfaces intended to be flat and parallel to each other but which, e.g., because of manufacturing tolerances or because of manufacturing processes, may slightly present a curvature or be slightly inclined with respect to each other.

A "measurement chamber" is a recess intended for receiving a volume of liquid approximately corresponding to its inner volume and adapted for the photometric measurement of this liquid. The liquid may be introduced in one or more steps. For example, a volume of sample approximately corresponding to the volume of the recess may be introduced for being analyzed as such. Alternatively, smaller volumes of one or more samples and one or more reagents may be introduced so that the total volume approximately corresponds to the volume of the recess. Thus the measurement chamber is a liquid confinement chamber designed for receiving a pre-defined total volume of liquid and is optimized for operating with such a predefined volume of liquid. According to a typical embodiment the measurement chamber has a volume that is less than about 50 μL and more typically in a range of between about 20 and about 30 μL, e.g., about 25 μL.

Ideally, the liquid fills the measurement chamber with a flat upper surface laying in the plane B-B. The term "approximately" here refers to deviations from this ideal status, wherein due to surface energy, i.e., capillary forces, a meniscus is typically formed. The meniscus may be below or above the plane B-B depending on the wettability of the cuvette material by the liquid and thus depending on the liquid and on the cuvette material. Thus, either a slightly smaller volume or larger volume of liquid may be introduced with respect to the volume of the recess. One effect of the design of the cuvette according to this embodiment the invention is to minimize such deviations of the location of the meniscus. This means that the effect is to minimize the meniscus such that the minimum or maximum of the meniscus is closer to the plane B-B and thus even volumes of liquid less than about 50 μL can be reliably subjected to photometric measurement.

This is achieved by designing the cuvette such that, at least in the plane B-B the lower inner edges are sharp or comprise fillets having a first radius, and in the plane A-A the first annular cross-section has a second radius or the upper inner edges comprise fillets having a second radius, the second radius being larger than the first radius. Further, the transition inner edges comprise fillets having a gradually increasing radius passing from the sharp edges or the first radius of the lower inner edges in the plane B-B to the second radius of the first annular cross-section or of the upper inner edges in the plane A-A.

The term "sharp" means that the lower walls converge into a line edge or into an only minimally rounded edge, e.g., due to manufacturing tolerances or processes. Since, at the microscopic level there is always a first radius at the lower inner edges, according to the present embodiment an edge is regarded to be sharp when it has a radius below 0.01 mm. The effect of being sharp is an increased capillary effect, i.e., an enhanced tendency of the typically used liquids (aqueous solutions) to rise along the edge. Thus, the sharper the edge is the higher its capillary effect. The opposite is true for smooth or curved edges, i.e., for edges with larger radius.

The term "fillet" is here used to indicate a more discernible curvature at the edge having a certain radius like if material was added on an imaginary edge line to make the edge smoother rather than sharp. The presence of a fillet is sometimes unavoidable for manufacturing or cost reasons.

The term "radius" of an edge or a fillet refers to the radius of an osculating circle symmetrically laying between two adjacent walls and whose curvature matches the curvature of the edge most tightly. In particular, it is the radius of that circle, which among all substantially tangent circles at that given position has substantially the same curvature as the edge.

In order to achieve the above mentioned effect, the embodiment is configured such that the lower inner edges, at least in the plane B-B, are sharp or, if filleted, that the fillet has a minimal first radius.

Also in accordance with an embodiment, the first cross-section in the plane A-A is configured such that it is larger than the second cross-section in the plane B-B, and that the second radius is larger than the first radius. In this way, an abrupt transition zone can be created between the plane B-B and the plane A-A, wherein the transition inner edges comprise fillets having a gradually increasing radius passing from the plane B-B to the plane A-A within a short distance.

The more abrupt the transition is, i.e., the stronger the change in radius and the shorter the distance in which the radius changes, the stronger the surface energy is, i.e., the energy barrier at the edges in the plane B-B, preventing the liquid to rise above the plane B-B. Also, the meniscus is forced to remain symmetric such that tilting of the liquid surface is prevented. Thus, according to a typical embodiment, the distance between the plane A-A and B-B is short compared to the distance between the plane A-A and the upper open top portion, and compared to the distance between the plane B-B and the lower closed bottom portion. However, the plane A-A is typically always different from the plane B-B, that is the distance between the plane A-A and the plane B-B is typically always greater than zero.

In practice, when adding a volume of liquid to the measurement chamber that is smaller than the volume of the chamber, the liquid will rise quickly along the sharp edges and will stop at the intersection with plane B-B. By adding more liquid, the minimum of the meniscus will rise approaching more and more the plane B-B while the edge of the meniscus will remain confined in the plane B-B rather than continuing to rise along the transition inner edges and then along the upper inner edges. By adding even more liquid, an energy balance is reached, above which the barrier of the surface energy is broken and the liquid will continue to rise. The meniscus may even rise above the plane B-B before this balance is reached. However, designing the cuvette so that when a predefined-volume of liquid is introduced, a meniscus is formed which is just below the plane B-B and an energy level is reached which is sufficiently below the energy barrier, is typical. For example, the cuvette may be designed such that when a predefined-volume of liquid is introduced the minimum of the meniscus is stopped at a distance from the plane B-B which is less than about 20% of the distance between the plane B-B and the lower closed bottom portion.

Fixing of the meniscus at plane B-B prevents that liquid volume is lost into the transition zone and upper part, which would reduce the volume in the lower measurement chamber, which is needed for the photometric measurement. Measurement thus can be enabled even with smaller volumes of liquid.

The energy level is such that losses of liquid from the measurement chamber are minimized even when moving the cuvette and/or when mixing the liquid in the measurement chamber, e.g., by stirring, by using ultrasound or shaking. Configuring the plane A-A and the plane B-B in different planes respectively, in other words by having an inclined transition zone, has the further advantage that liquid eventually escaping from the measurement chamber, e.g., during mixing, can more easily return to the measurement chamber. If the transition zone was flat, that is if the plane A-A and the plane B-B were on the same plane, liquid that escapes from the measurement chamber onto the flat transition zone would be retained there and thus permanently lost without the possibility to return to the measurement chamber.

According to one embodiment, the upper part of the cuvette has a tapered shape with a cross-section, which is gradually increasing from the plane A-A to the top open portion.

According to another embodiment, the upper inner edges comprise fillets having a constant second radius between the plane A-A and the top open portion.

According to yet another embodiment, the upper inner edges comprise fillets having a second radius, which is gradually increasing from the plane A-A to the open top portion.

According to still yet another embodiment, the open top portion has a substantially circular or elliptical cross-section.

The cross-section of the upper part and/or the size of the second radius above the plane A-A may play a role other than that described above with relation to the surface energy. This role may be related to e.g., easier and/or less expensive manufacturing or to more convenient use of the cuvette, e.g., when introducing a liquid or when handling a cuvette.

According to another embodiment, the lower front wall and the lower back wall have a substantially rectangular area comprising corners with a curved shape in proximity of the lower closed bottom portion.

According to yet another embodiment, at least the lower front wall and the lower back wall are optically transparent.

According to still yet another embodiment, the cuvette in proximity of the open top portion comprises at least one lip projecting outwards of the cuvette body. This lip may be convenient when handling the cuvette and/or for holding the cuvette in a cuvette holding position of an optical system and/or for aligning the cuvette in an optical system.

According to another embodiment, a cuvette is manufactured in one piece of injection molded polymeric material.

According to yet another embodiment, a product comprising a plurality of cuvettes, arranged, e.g., as an array of cuvettes next to each other side by side, joined, e.g., by a strip or common lip in the upper part, is manufactured in one piece of injection molded polymeric material.

In accordance with yet another embodiment of the present invention, an optical system for photometric measurement of liquids is provided. The system comprises a plurality of cuvettes according to any of the above embodiments, a light source providing a light beam, and an optical detector. The system further comprises a control unit that's configured to bring one cuvette at a time in optical alignment with the light source and the detector so that the lower front wall faces the light source and the lower back wall faces the optical detector.

According to an embodiment the present invention, an optical system is either a separate unit or an integrated component or module within an analytical instrument. Particularly, the optical system makes it possible to guide light in a controlled manner through a sample located in the measurement chamber of the cuvette, and to measure changes in optical transmission, such as absorbance and scattering, for the optical analysis of analytes present in the sample. The optical system may be however configured to carry out in addition other spectroscopic measurements. It may also entail temporally static measurements, time resolved measurements, or both.

The system may further comprise a cuvette holding unit for holding comprising at least one cuvette holding position. The cuvette holding unit may be embodied as a conveyor, e.g., a linear or rotor-like conveyor, moving in at least one direction or as a robotic arm capable of performing movements, driven by one or more electrical motors. According to one embodiment, the cuvette holding unit comprises an array of cuvette holding positions, the cuvette holding positions being located in the optical path one at a time according to an established assay sequence. According to another typical embodiment, the cuvette holding unit is assembled as a rotor comprising a plurality of cuvette holding positions to receive a plurality of cuvettes and to bring one cuvette at a time in the optical path, i.e., in optical alignment with the light source and the detector.

The optical system is particularly suitable for analyzing biological samples. Samples are typically liquid solutions in which one or more analytes of interest can be potentially found, such as body fluids like blood, serum, plasma, urine, milk, saliva, cerebrospinal fluid, etc. . . . . Samples may be analyzed as such or after being diluted with another solution or after having being mixed with reagents, e.g., to carry out one or more diagnostic assays like, e.g., clinical chemistry assays and immunoassays. The optical system may advantageously be used in the performance of scattering assays to detect the result of a chemical or biological reaction or to monitor the progress of a chemical or biological reaction, e.g., in a coagulation assay, agglutination assay, turbidimetric assay.

A light source according to an embodiment of the invention is a unit within the optical system capable of emitting a light beam in a usable wavelength range. The term "usable" refers to a selected wavelength or wavelength range, at which light guided through a sample can be used to measure analyte concentrations present in the sample.

The light source comprises at least one light emitting element. A light emitting element is an electric powered radiation source such as, for example, an incandescent lamp, an electroluminescent lamp, a gas discharge lamp, a high-intensity discharge lamp, a laser.

According to one embodiment the at least one light emitting element is for example a halogen lamp, which like all incandescent light bulbs, produces a continuous broad spectrum of light, from near ultraviolet to far infrared.

According to another embodiment the at least one light emitting element is a light emitting diode or "LED".

According to another embodiment the light beam has a curved shape divided in four symmetric sectors, each sector having a shape substantially matching the shape of the corners of the cuvette in proximity of the lower closed bottom portion.

According to yet another embodiment the light beam has an area of intersection with the lower front wall which is between about 2 and about 10 times smaller than the area of the lower front wall.

An optical detector according to an embodiment of the present invention is a photodetector, which is a device that converts electro-magnetic energy into an electrical signal, including both single element and multi-element or array optical detectors. Thus an optical detector is a device capable of monitoring an optical electro-magnetic signal and providing an electrical output signal or response signal relative to a baseline signal indicative of the presence and/or concentration of an analyte in a sample being located in the optical path. Such devices can include, for example, photodiodes, including avalanche photodiodes, phototransistors, photoconductive detectors, linear sensor arrays, CCD detectors, CMOS optical detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrating circuit. Suitable pre-preamplifiers include integrating, transimpedance, and current gain (current mirror) pre-amplifiers. According to one embodiment, the detector is of the CCD or CMOS type. According to another embodiment the detector is of the photodiode or PMT type.

The control unit may be embodied as programmable logic controller running a computer-readable program provided with instructions to perform operations in accordance with a process operation plan.

An analytical instrument according to the present invention is an apparatus assisting users with the detection, e.g., qualitative and/or quantitative optical evaluation of samples for diagnostic purpose. Examples of such an instrument are: a clinical chemistry analyzer, a coagulation chemistry analyzer, an immunochemistry analyzer, a urine analyzer, either as self-standing instrument or module within a system comprising a plurality of said modules, used to detect the result of chemical or biological reactions or to monitor the progress of chemical or biological reactions.

In particular, the instrument may comprise units assisting with the pipetting, dosing, mixing of samples and/or reagents, units for loading and/or unloading and/or transporting and/or storing sample tubes or racks comprising sample tubes, units for loading and/or unloading and/or transporting and/or storing reagent containers or cassettes. The analyzer may also comprise identification units comprising sensors, e.g., barcode readers. Alternative technologies such as RFID may also be used for identification.

According to another typical embodiment the instrument further comprises a sample receiving unit for receiving samples to be assayed. Samples may be received for example in the form of tubes, e.g., blood collection tubes, or smaller tubes or vessels comprising sample aliquots. Samples may be arranged in single carriers or holders or racks for multiple samples.

According to another typical embodiment the instrument further comprises a reagent holding unit for holding reagents to perform the assays. Reagents may be arranged for example in the form of containers or cassettes containing individual reagents or group of reagents, placed in appropriate receptacles or positions within a storage compartment or conveyor.

According to yet another typical embodiment the instrument further comprises a cuvette feeding unit for feeding cuvettes to the cuvette holding unit.

According to still yet another typical embodiment the instrument further comprises one or more liquid processing units, e.g., a pipetting unit, to deliver samples and/or reagents to optical cuvettes. The pipetting unit may comprise a reusable washable needle, e.g., a steel needle, or disposable pipette tips. Typically, the pipetting unit is operatively coupled to an automated positioning device for moving the pipette tip or needle with respect to the instrument and, e.g., may be mounted to a transfer head that can be moved in two directions of travel in a plane, e.g., by means of guiding rails and a third direction of travel orthogonal to the plane, e.g., by means of a spindle drive.

The instrument may further comprise one or more incubation units for maintaining sample/reagent mixtures at a certain temperature during reaction, wash stations for washing pipette tips or needles, mixing paddles, etc. . . . .

The instrument may further comprise mixing one or more mixing units, comprising, e.g., a shaker to shake a cuvette comprising a liquid or a mixing paddle to mix liquids in a cuvette or reagent container or an ultrasound generator.

According to a typical embodiment the instrument can be set up for controlling pipetting in the lower measurement chamber of a pre-defined volume of liquid or for adding one or more liquids until a pre-defined volume of liquid is reached, which nearly corresponds to the inner volume of the lower measurement chamber. The fact that the liquid boundaries are confined at the plane B-B enables to cope with pipetting and/or manufacturing tolerances. For example, even if a volume of liquid slightly larger than the volume of the lower measurement chamber is added, the center of the meniscus would rise above the plane B-B but its boundaries would still remain at the plane B-B.

The present invention also refers to a method for photometric measurement of liquids. The method comprises the step of holding a cuvette according to any of the above embodiments in optical alignment with the light source and the detector so that the lower front wall faces the light source and the lower back wall faces the optical detector. The method further comprises the step of moving the cuvette along an axis parallel to the lower front wall while performing a photometric measurement.

The method may comprise the step of introducing in the cuvette, and in particular in the measurement chamber, a pre-defined volume of liquid or to add one or more liquids until a pre-defined volume of liquid is reached. This step is typically carried out automatically by means of the liquid processing unit.

According to a typical embodiment the method comprises the step of bringing one cuvette at a time in optical alignment with the light source and the detector so that the lower front wall faces the light source and the lower back wall faces the optical detector. Typically, a holding unit embodied, e.g., as a rotor-like conveyor, is used to bring by rotation one cuvette at a time in optical alignment with the light source and the detector. The rotor may rotate continuously so that cuvettes are moving along an axis parallel to the lower front wall while performing a photometric measurement. By stopping the rotor every time for a new cuvette, achieving a reproducible alignment would be more critical and time consuming, e.g., due to induced vibration of the rotor. This would lead to longer measurement/controlling times and smaller accuracies due to positioning-variations.

On the other hand, by continuously moving the rotor the time available for the measurement is limited. It is therefore important to maximize the measurement volume in order to obtain an acceptable photometric signal.

The cuvette and system of the present invention are optimized for maximizing the measurement volume given a pre-defined small volume of liquid. The "measurement volume" is defined as the volume of liquid in the measurement chamber which is actually exposed to the light beam during the time of a photometric measurement. This is given by the area of intersection between the light beam and the lower front wall times the distance between the lower front wall and lower back wall. The distance between the lower front wall and lower back wall is also called optical path. If the cuvette is moving during the measurement, then the measurement volume is given by the area scanned by the light beam during the time of the measurement times the optical path.

In order to perform a reliable measurement, one should ensure that during the time of measurement the light beam will intersect the lower front wall sufficiently far away from the edges and the meniscus, which might interfere with the measurement. In order to make that sure, there are factors, which need to be taken into account, such as for example positioning/alignment tolerances of a cuvette in the optical system, manufacturing tolerances, possible presence of fillets in the measurement chamber. All these factors, together with a minimal distance from the lower closed bottom portion at which the minimum of the meniscus can be found, define a "tolerance measurement window".

The embodiments of the present invention are configured to maximize the tolerance window, such as, to enable to maximize the measurement volume within the tolerance window for a pre-defined volume of liquid.

According to one aspect of the invention, the meniscus is stabilized and nearly flattened, as described above, in proximity of the plane B-B, thus increasing the distance of the minimum of the meniscus from the lower closed bottom portion, thus increasing the tolerance measurement window and thus enabling to increase the measurement volume within the tolerance window. By having lower inner edges, which are sharp or comprise fillets having a small first radius, has the further effect to minimize reduction of the tolerance window thus enabling to increase the measurement volume.

The light beam typically has a circular or elliptical cross-section. According to another aspect of the invention, the detection volume is further increased by designing the lower front wall and lower back wall such that the corners in proximity of the lower closed bottom portion have a shape that substantially matches the shape of one sector of the light beam used in the optical system. Further, the lower front wall and lower back wall are designed such that they have an area, which is typically between about 2 and about 10 times larger than the area of intersection between the lower front wall and the light beam. In this way a larger light beam may be used and by moving the cuvette with respect to the light beam the area scanned by the light beam during the time of measurement may be increased, thus the measurement volume may be maximized.

Further improvements may be obtained by using an array of cuvettes arranged side by side next to each other and manufactured in one piece. This piece may have, e.g., the form of a segment adapted to fit on a conveyor, e.g., rotor-like conveyor of the optical system. In this way, tolerances due to cuvette positioning/alignment within the optical system may be minimized. Thus variations of the position of the tolerance measurement window for each measurement and for each cuvette are minimized.

In order that the embodiments of the invention may be more readily understood, reference is made to the following examples, which are intended to illustrate the invention, but not limit the scope thereof.

FIG. 1 shows one example of a cuvette 100 according to an embodiment of the invention. In particular, FIG. 1a shows a top view of the cuvette 100, FIG. 1b shows a perspective view of the cuvette 100, FIG. 1c shows a front view of the cuvette 100, FIG. 1d shows a cross-section of the cuvette 100 through the plane A-A of FIG. 1c, and FIG. 1e shows a cross-section of the cuvette 100 through the plane B-B of FIG. 1c. The drawings of FIGS. 1a to 1e as well as the following figures are not to scale for clarity of illustration.

The cuvette 100 comprises a body 10 having outer walls 11 and an inner space 12 for receiving liquids. The body 10 comprises an upper part 20. According to one embodiment, the upper part 20 comprises an upper open top portion 21 for allowing liquids to be introduced into the cuvette 100, an upper front wall 22, an upper back wall 23, two upper side walls 24, 25, said upper walls 22, 23, 24, 25 forming four upper inner edges 26 and an upper open bottom portion 27 with a first substantially rectangular cross-section in the plane A-A.

The body 10 further comprises a lower measurement chamber 30. The lower measurement chamber 30 comprises a lower closed bottom portion 31, a lower front wall 32, a lower back wall 33, two lower side walls 34, 35, said lower walls 32, 33, 34, 35 forming four lower inner edges 36 and a lower open top portion 37 with a second substantially rectangular cross-section in a plane B-B smaller than the first substantially rectangular cross-section in the plane A-A. The lower front wall 32 and the lower back wall 33 are substantially planar and parallel to each other.

The body 10 further comprises a transition zone 40 between the plane A-A and the plane B-B, i.e., between the upper part 20 and the lower measurement chamber 30. The transition zone 40 comprises four transition inner edges 46 connecting the four lower inner edges 36 to the four upper inner edges 26.

The lower inner edges 36 comprise fillets having a first radius R1. In the plane A-A, the upper inner edges 26 comprise fillets having a second radius R2, the second radius R2 being larger than the first radius R1. The transition inner edges 46 comprise fillets having a gradually increasing radius passing from the first radius R1 in the plane B-B to the second radius R2 in the plane A-A.

The cuvette 100 has also a third substantially rectangular cross-section in the plane of the upper open top portion 21, which is larger than the first substantially rectangular cross-section in the plane A-A. Thus the upper part 20 has a tapered shape with a cross-section, which is gradually increasing from the plane A-A to the top open portion 21, and the upper inner edges 26 comprise fillets having a second radius R2, which is gradually increasing from the plane A-A to the open top portion 21.

The cuvette 100 further comprises in proximity of the upper open top portion 21 a lip 28 projecting outwards of the cuvette body 10 as a frame. This lip 28 is convenient for handling and holding the cuvette 100 in an analytical instrument.

The lower front wall 32 and the lower back wall 33 are optically transparent.

Figure 2:
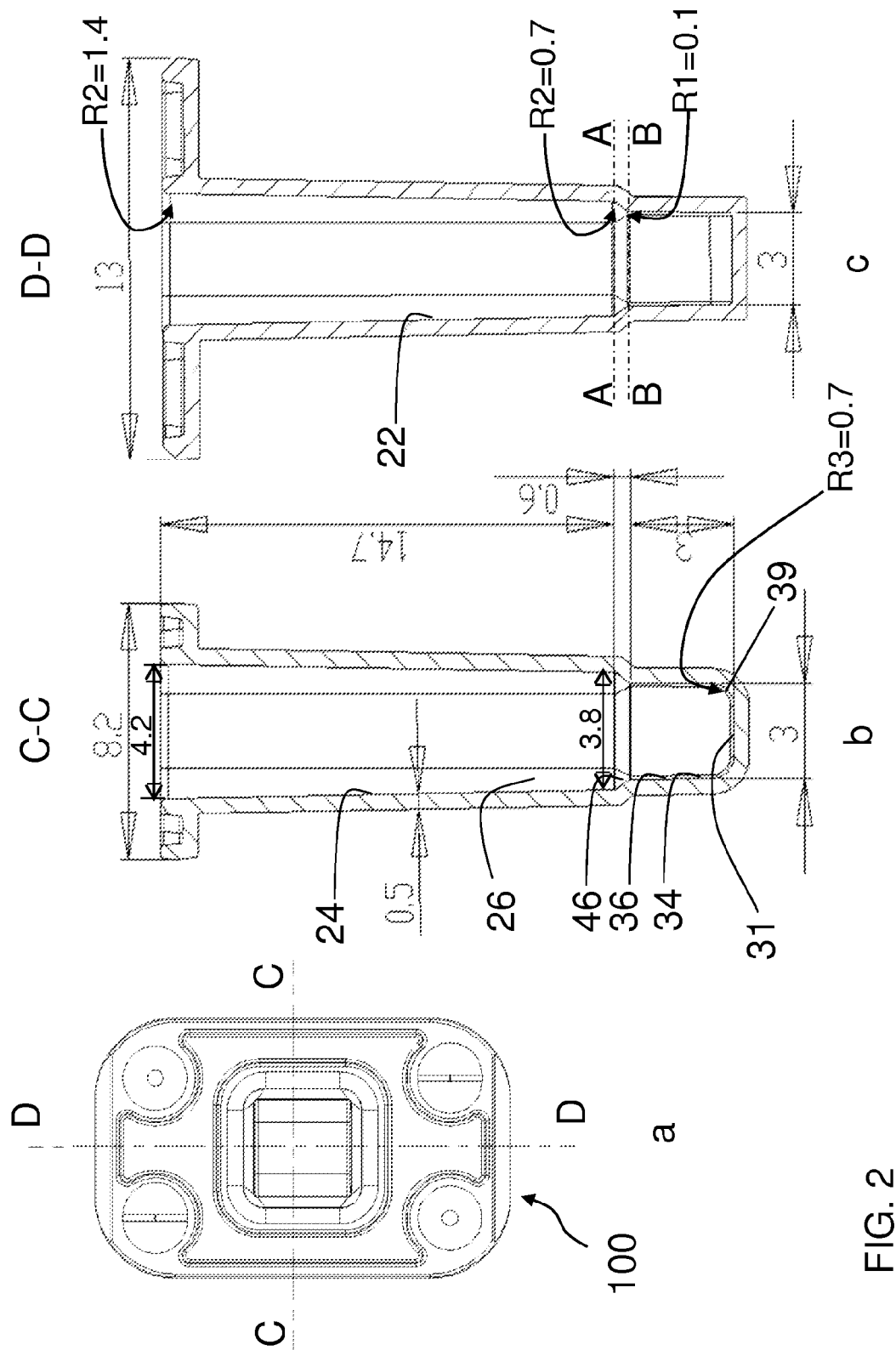
FIGS. 2a to 2c provide an example of dimensions (in millimeters) for the cuvette of FIG. 1.

FIG. 2 provides some of the dimensions (in millimeters) for the cuvette of FIG. 1. In particular, FIG. 2a shows the same top view of the cuvette 100 of FIG. 1a. FIG. 2a shows a cross-section of the cuvette 100 through a vertical plane C-C passing from the upper top open portion 21 to the lower closed bottom portion 31 through the middle of the body 10. FIG. 2b shows a cross-section of the cuvette 100 through a vertical plane D-D passing from the upper top open portion 21 to the lower closed bottom portion 31 through the middle of the body 10 and orthogonal to plane C-C. The thickness of the walls of the cuvette body 10 is substantially constant and about 0.5 mm.

The cuvette 100 has a first substantially squared cross-section in the plane A-A with a width of about 3.8 mm, a second substantially squared cross-section in the plane B-B with a width of about 3 mm, and a third substantially squared cross-section in the plane of the upper open top portion 21 with a width of about 4.2 mm. The distance from the plane A-A to the upper top open portion 21 is about 14.7 mm. The distance from the lower closed bottom portion 31 to the plane B-B is about 3 mm. The distance between the plane A-A and the plane B-B is about 0.6 mm. The lower inner edges 36 have fillets with a first radius R1 of about 0.1 mm from the plane B-B to the lower closed bottom portion 31. The upper inner edges 26 have fillets with a second radius R2, which is gradually increasing from the plane A-A to the open top portion 21. The second radius R2 is about 0.7 mm in the plane A-A and about 1.4 mm in the plane of the upper open top portion 21.

Thus, the transition inner edges 46 connecting the four lower inner edges 36 to the four upper inner edges 26 have fillets with a radius, which is gradually increasing from the plane B-B to the plane A-A passing from about 0.1 mm to about 0.7 mm within a short distance of about 0.6 mm between the plane B-B and the plane A-A. This is an example of an abrupt transition, i.e., of a strong change in radius in a short distance, responsible for a strong surface energy, i.e., strong energy barrier, at the lower inner edges in the plane B-B. In general, a transition may be considered to be abrupt if the transition inner edges 46 connecting the four lower inner edges 36 to the upper part 20 have fillets with a radius, which is gradually increasing from the plane B-B to the plane A-A passing from a first radius R1, which is smaller than 1 mm to a second radius R2 of up to several mm, e.g., up to the radius of the cross-section 27 in case of annular, e.g., circular, cross-section 27, within a distance greater than zero and up to about 5 mm between the plane B-B and the plane A-A. In the embodiment of FIG. 2, the lower front wall 32 and lower back wall 33 have a substantially rectangular area and comprise corners 39 with a curved shape in proximity of the lower closed bottom portion 31, having a radius R3 of about 0.7 mm.

With these dimensions the volume of the lower measurement chamber 30 is about 25 µL.

Figure 3:
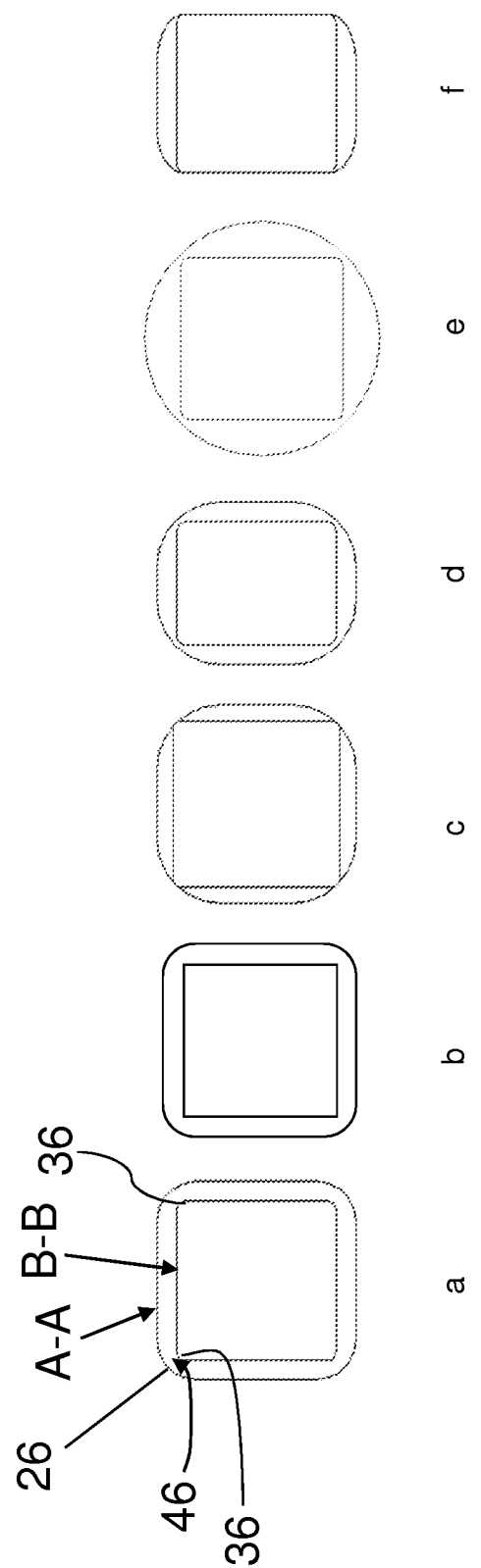
FIGS. 3a to 3f show schematically variants of the cuvette of FIG. 1 with reference to the geometries of cross-sections A-A and B-B.

FIG. 3 shows schematically variants of the cuvette 100 with reference to the geometries of the cross-sections A-A and B-B. In particular, FIG. 3a shows the embodiment of FIG. 1 and FIG. 2 for comparison. FIG. 3b shows an alternative embodiment wherein the lower inner edges 36 are sharp, although more difficult to produce. In FIG. 3c the cross-section of the plane A-A is larger than the cross-section of the plane B-B only between the edges 26,36. FIG. 3d shows cross-sections of elongated rectangular shape. In FIG. 3e the cross-section in the plane A-A is substantially circular while the cross-section in the plane B-B is substantially squared. In FIG. 3f the cross-section of the plane A-A is larger than the cross-section of the plane B-B only between two opposite edges. Of course any combinations of the geometries from the above examples are possible. Also, cross-sections in the plane A-A and B-B may be non-concentric and/or non-symmetric. The edges may have fillets with rounded circular or elliptical radius. All these variants may in turn be combined with different geometries of the cross-section in the plane of the top open portion 21, which may be substantially rectangular or annular (not shown).

Figure 4:
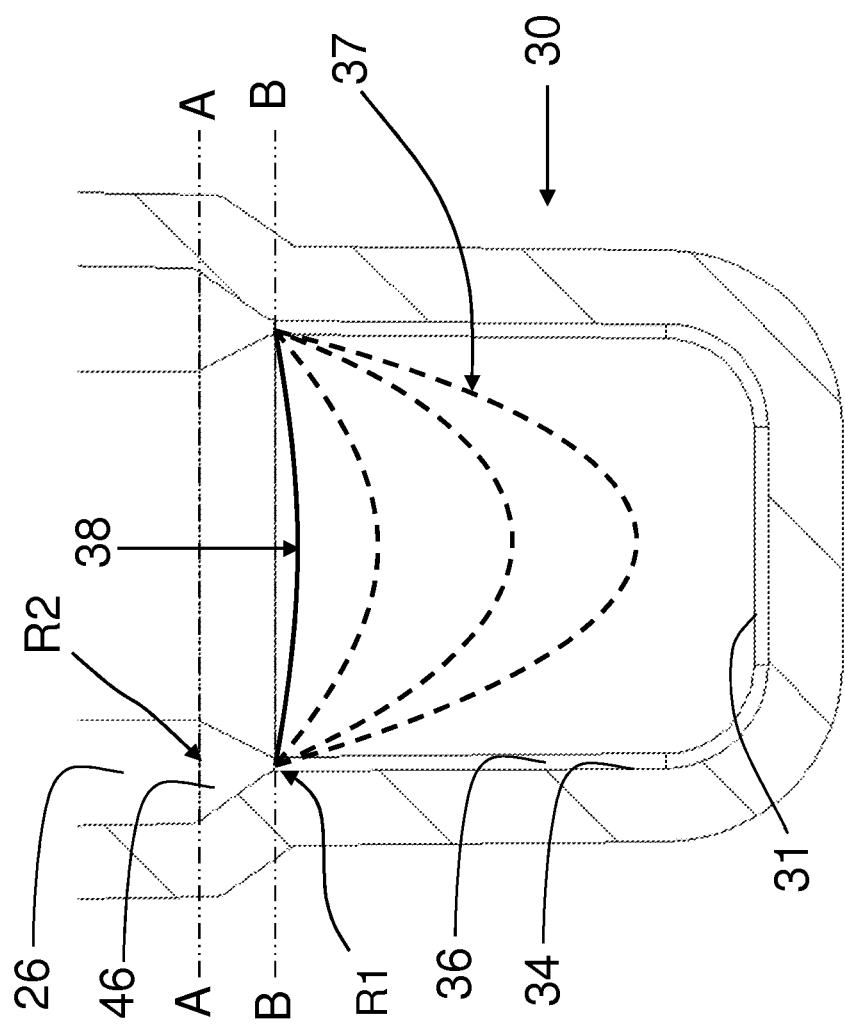
FIG. 4 shows schematically the effect of the geometry of the cuvette of FIG. 1 on the liquid meniscus.

FIG. 4 shows schematically the effect of the geometry of the cuvette 100 of FIG. 1 on the liquid meniscus 37. In practice, when adding a volume of liquid to the lower measurement chamber 30 that is less than the inner volume of the chamber 30, the liquid will rise (i.e., quickly) along the lower inner edges 36 due to the small radius R1, and will stop at the intersection with plane B-B. By adding more liquid, the minimum 38 of the meniscus 37 will rise approaching more and more the plane B-B while the edge of the meniscus 37 will remain confined in the plane B-B rather than continuing to rise along the transition inner edges 46. Thus the cuvette 100 is designed so that when a predefined-volume of liquid, e.g., 23-25 µL, is introduced in the lower measurement chamber 30 having an inner volume of about 25 µL, a meniscus 37 is formed, whose minimum 38 is just below the plane B-B, and thus the volume of liquid nearly corresponds to the inner volume of the lower measurement chamber 30. In this way it is prevented that liquid is lost in the transition zone 40 and upper part 20 and it is made possible to perform a reliable photometric measurement even with smaller volumes of liquids.

Figure 5:
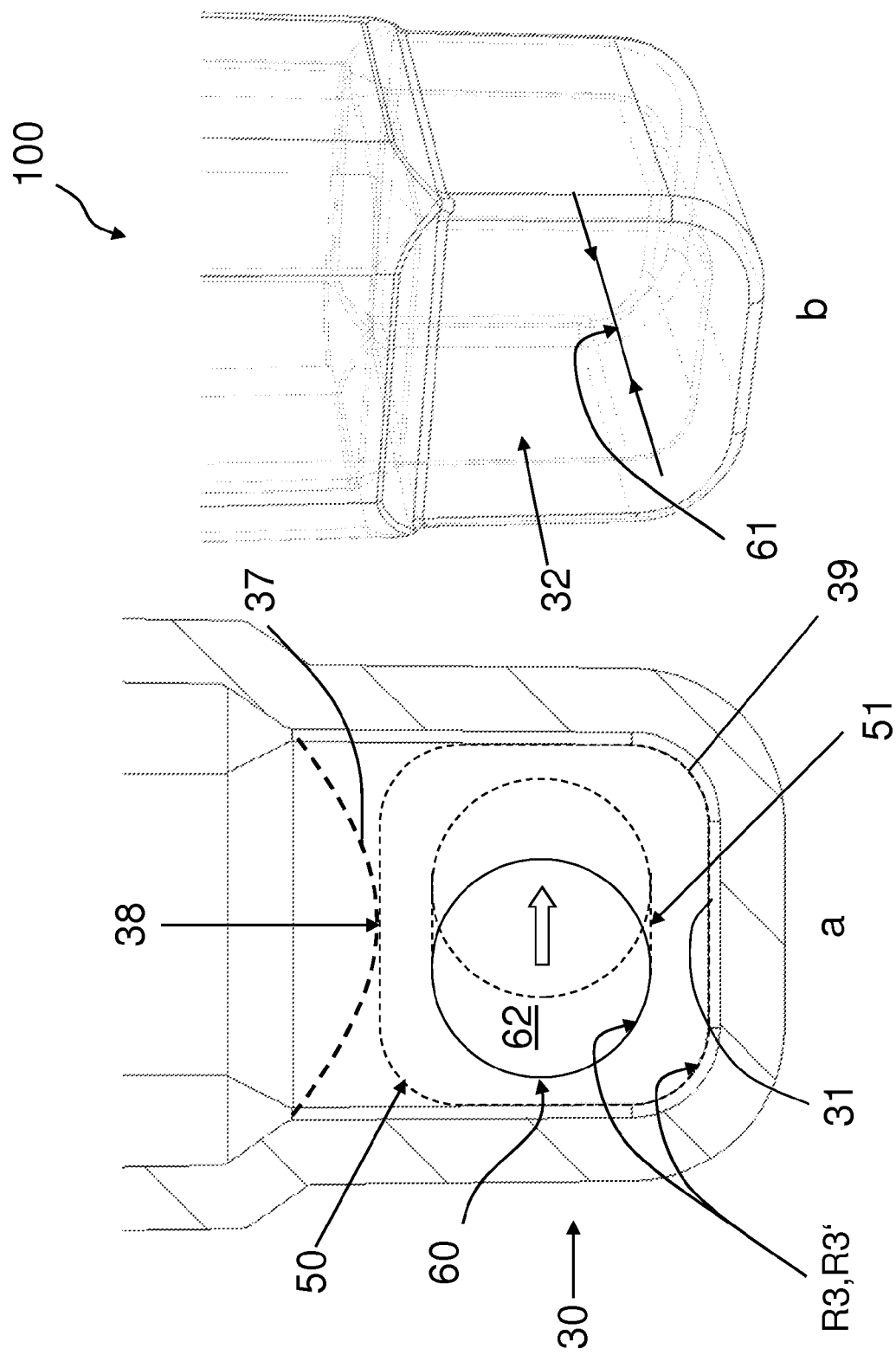
FIGS. 5a and 5b show the relationship between tolerance window and measurement volume for the cuvette of FIG. 1.

FIG. 5 shows the relationship between tolerance measurement window 50 and measurement volume for the cuvette 100 of FIG. 1. If the cuvette 100 is moving during the measurement, the measurement volume is given by the area 51 scanned by the light beam 60 at the intersection between the light beam 60 and the lower front wall 32 times the optical path 61, which is the distance between the lower front wall 32 and lower back wall 33, i.e., 3 mm in this example. In order to perform a reliable measurement, care should be taken such that during the time of measurement the light beam will intersect the lower front wall sufficiently far away from the edges and the meniscus, which might interfere with the measurement. During the measurement, factors need to be taken into account, such as, for example, positioning/alignment tolerances of the cuvette 100 in an optical system, manufacturing tolerances, the presence of fillets in the measurement chamber 30, and the actual position of the meniscus 37 with its minimum 38. All these factors define the "tolerance measurement window" 50. This means that the position of the tolerance measurement window 50 may change for each measurement and for each cuvette 100. However the area 51 scanned by the light beam 60 should fall within the tolerance measurement window 50 in order to have a reliable and reproducible measurement. Having fixed the volume of the liquid and the optical path length 61, it is also typical to have the area 51 as large as possible in order to obtain a larger measurement signal and thus higher sensitivity. The design of the cuvette 100 contributes to raising the minimum 38 of the meniscus 37. By having lower inner edges 36, which comprise fillets having a small first radius R1, contributes also to reduce the influence of the fillets on the size of the tolerance window 50. This enables to increase the area 51 scanned by the light beam 60 while still making sure that the area 51 falls within the tolerance measurement window 50.

In accordance with another embodiment, the lower front wall 32 and lower back wall 33 can be configured such that they have corners 39 in proximity of the lower closed bottom portion 31 with a shape, which substantially matches the shape of one sector of the light beam 60, e.g., by having the radius R3 of said corners 39 substantially matching the radius R3' of the light beam 60, in this case about 0.7 mm. Optimum results are achieved by designing the lower front wall 32 and lower back wall 33 such that they have an area, which is between about 2 and about 10 times larger than the area 62 of intersection between the lower front wall 32 and the light beam 60. In this case, the lower front wall 32 and lower back wall 33 are designed such that they have an area, which is between about 5 and about 6 times larger than the area 62 of intersection between the lower front wall 32 and the light beam 60.

Figure 6:
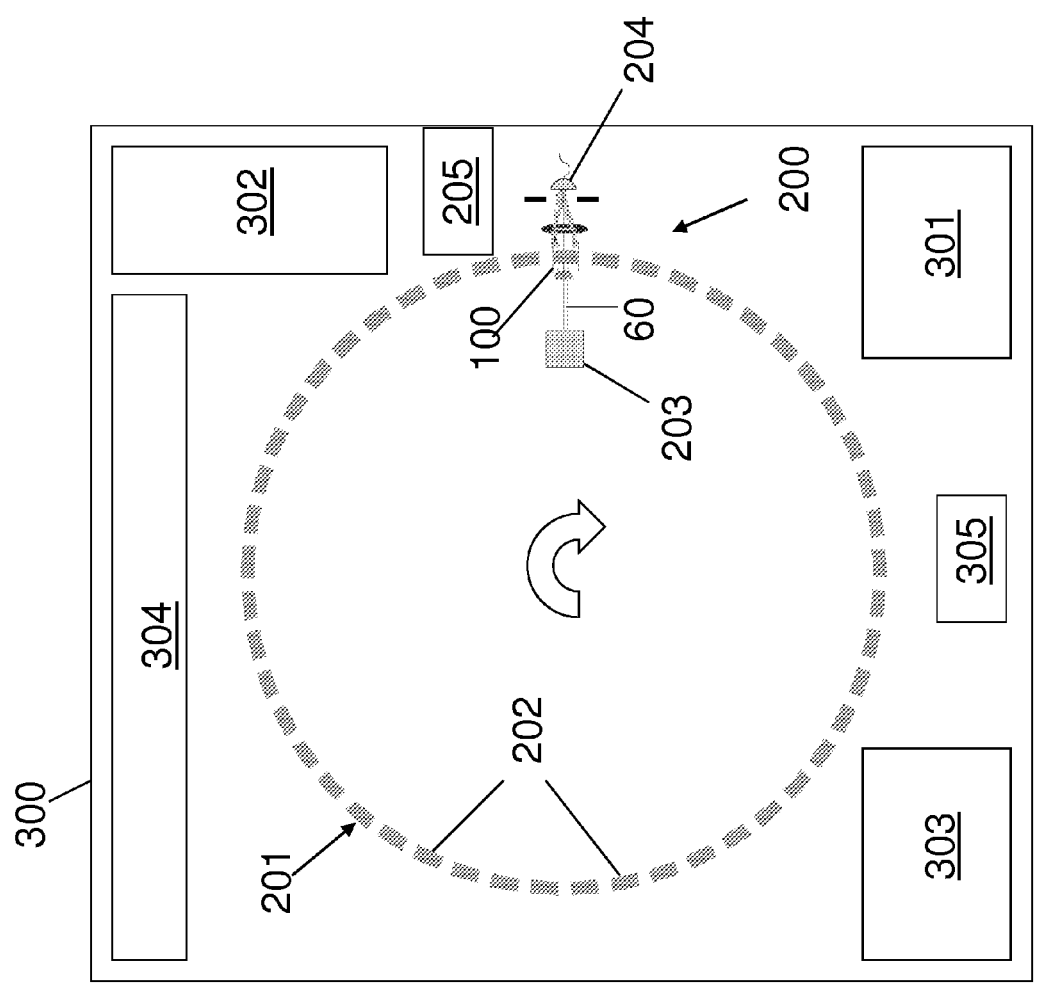
FIG. 6 shows schematically an analytical instrument comprising an optical system for photometric measurement of liquids.

FIG. 6 depicts schematically an analytical instrument 300 comprising an optical system 200 for photometric measurement of liquids. The optical system 200 comprises a light source 203 providing a light beam 60, an optical detector 204, a cuvette holding unit 201 arranged as a rotor comprising an array of cuvette holding positions 202 and a control unit 205 configured to bring one cuvette 100 at a time in optical alignment with the light source 203 and the optical detector 204 so that the lower front wall 32 faces the light source 203 and the lower back wall 33 faces the optical detector 204. The rotor is arranged to rotate and to move a cuvette 100 along an axis parallel to the lower front wall 32 while performing a photometric measurement. The instrument 300 further comprises a sample receiving unit 301 for receiving sample tubes (not shown) comprising samples to be assayed. The analytical instrument 300 further comprises a reagent holding unit 302 for holding reagent containers (not shown) comprising reagents to perform the assays. The instrument 300 further comprises a cuvette feeding unit 303 for feeding optical cuvettes 100 to the cuvette holding unit 201. The analytical instrument 300 further comprises a liquid processing unit 304, such as at least one pipetting unit, to deliver samples and/or reagents to cuvettes 100. Cuvettes 100 may be temporarily removed from the rotor 201 for addition of samples and/or reagents or for mixing operations by a mixing unit 305.

Obviously many modifications and variations of the present invention are possible in light of the above description. It is therefore to be understood, that within the scope of the appended claims, the invention may be practiced otherwise than as specifically devised.

It is noted that terms like "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

What is claimed is:

1. A cuvette for photometric measurement of liquids comprising:
   a body having outer walls and an inner space for receiving liquids, said body comprising
      an upper part comprising an upper open top portion and an inner surface having in a plane A-A a first annular or substantially rectangular cross-section with four upper inner edges, the upper inner edges extending from the plane A-A to the upper open top portion,
      a lower measurement chamber with an inner volume less than about 50 μL comprising a lower closed bottom portion, a lower front wall, a lower back wall, two lower side walls, said lower walls forming four lower inner edges and a lower open top portion with a second substantially rectangular cross-section in a plane B-B smaller than the first annular or substantially rectangular cross-section in the plane A-A, wherein at least the lower front wall and the lower back wall have portions which are substantially planar and substantially parallel to each other, and
      an abrupt transition zone between the upper part and the lower measurement chamber, extending between the plane A-A and the plane B-B and comprising four transition inner edges connecting the four lower inner edges to the upper part, wherein the plane A-A and the plane B-B are substantially perpendicular to the longitudinal axis of the cuvette, wherein the plane A-A is different from the plane B-B, and wherein
         at least in the plane B-B the lower inner edges are sharp or comprise fillets having a first radius,
         in the plane A-A the first annular cross-section has a second radius or the upper inner edges comprise fillets having a second radius, the second radius being larger than the first radius,
         the transition inner edges comprise fillets having a gradually increasing radius passing from the sharp edges or the first radius of the lower inner edges in the plane B-B to the second radius of the first annular cross-section or of the upper inner edges in the plane A-A.

2. The cuvette according to claim 1, wherein the upper part has a tapered shape with a cross-section, which is gradually increasing from the plane A-A to the top open portion.

3. The cuvette according to claim 1, wherein the upper inner edges comprise fillets having a constant second radius between the plane A-A and the upper open top portion.

4. The cuvette according to claim 1, wherein the upper inner edges comprise fillets having a second radius, which is gradually increasing from the plane A-A to the upper open top portion.

5. The cuvette according to claim 4, wherein the upper open top portion has an annular cross-section.

6. The cuvette according to claim 1, wherein the lower front wall and the lower back wall have a substantially rectangular area comprising corners with a curved shape in proximity of the lower closed bottom portion.

7. The cuvette according to claim 1, wherein at least the lower front wall and the lower back wall are optically transparent.

8. The cuvette according to claim 1 further comprising at least one lip projecting outwards of the cuvette body.

9. An optical system for photometric measurement of liquids comprising:
   a plurality of cuvettes according to claim 1,
   a light source providing a light beam,
   an optical detector, and
   a control unit configured to bring one cuvette at a time in optical alignment with the light source and the detector so that the lower front wall faces the light source and the lower back wall faces the optical detector.

10. The optical system according to claim 9, wherein the light beam has cross-section having a shape substantially matching the shape of the corners of the cuvette in proximity of the lower closed bottom portion.

11. The optical system according to claim 9, wherein the light beam has an area of intersection with the lower front wall which is between about 2 and about 10 times smaller than the area of the lower front wall.

12. An instrument for photometric measurement of liquids comprising an optical system according to claim 9 and a liquid processing unit, wherein the instrument is configured for controlling pipetting, in the lower measurement chamber of a cuvette, a pre-defined volume of liquid or for adding one or more liquids until a pre-defined volume of liquid is reached, which nearly corresponds to the inner volume of the lower measurement chamber.

13. A method for photometric measurement of liquids comprising the steps of:
   holding a cuvette according to claim 1 in optical alignment with a light source providing a light beam and a detector so that the lower front wall faces the light source and the lower back wall faces the optical detector, and
   moving the cuvette along an axis parallel to the lower front wall while performing a photometric measurement.

14. The method according to claim 13 further comprising the step of designing the lower front wall and lower back wall such that they have an area, which is between about 2 and about 10 times larger than an area of intersection between the lower front wall and the light beam used for detection, and the corners in proximity of the lower closed bottom portion have a shape, which substantially matches the shape of one sector of the light beam.

* * * * *